(12) United States Patent
Malocha et al.

(10) Patent No.: US 9,970,902 B2
(45) Date of Patent: May 15, 2018

(54) METHOD OF FORMING SURFACE ACOUSTIC WAVE TAG-BASED GAS SENSORS

(71) Applicant: University of Central Florida Research Foundation, Inc., Orlando, FL (US)

(72) Inventors: Donald Malocha, Winter Park, FL (US); Brian Fisher, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days. days.

(21) Appl. No.: 15/164,371

(22) Filed: May 25, 2016

(65) Prior Publication Data

US 2017/0254780 A1 Sep. 7, 2017

Related U.S. Application Data

(62) Division of application No. 13/780,098, filed on Feb. 28, 2013, now Pat. No. 9,383,340.

(51) Int. Cl.
*G01N 29/00* (2006.01)
*G01N 29/02* (2006.01)

(52) U.S. Cl.
CPC ..... *G01N 29/022* (2013.01); *G01N 2291/021* (2013.01); *G01N 2291/045* (2013.01); *G01N 2291/0423* (2013.01)

(58) Field of Classification Search
USPC .......................................... 427/58
See application file for complete search history.

(56) References Cited

U.S. PATENT DOCUMENTS

| 5,330,855 A * | 7/1994 | Semancik | B82Y 15/00 428/216 |
| 7,268,662 B2 * | 9/2007 | Hines | B82Y 15/00 338/28 |
| 7,777,625 B1 * | 8/2010 | Puccio | G06K 19/0672 340/539.1 |

OTHER PUBLICATIONS

Khabiboulakh Katsiev, "Study of Tin Oxide: Surface Properties and Palladium Adsorption", Tulane University, School of Science and Engineering, Dissertation Abstracts International, vol. 70-02, Section B, p. 1085, 150 pages, 2008.

(Continued)

*Primary Examiner* — Brian K Talbot
(74) *Attorney, Agent, or Firm* — Jetter & Associates, P.A.

(57) ABSTRACT

A method for fabricating a sensor system includes providing a surface acoustic wave (SAW) tag on a substrate including a detector bank of reflectors at one end to generate a detector SAW responsive to an interrogation signal, a reference bank of reflectors at an opposite end of the substrate to generate a reference SAW responsive to the interrogation signal, and a transducer between the detector and reference banks of reflectors for receiving the interrogation signal and transmitting the detector and reference SAW from the detector and the reference banks of reflectors in response. A hydrogen gas sensor is formed on the substrate in a propagation delay path (delay path) between the detector bank of reflectors and the transducer to modulate propagation parameters of the detector SAW in response to sensing hydrogen gas. The forming includes depositing a $SnO_2$ film then depositing a Pd film onto the $SnO_2$ film.

10 Claims, 8 Drawing Sheets

(56) References Cited

OTHER PUBLICATIONS

Jacqueline H. Hines, Applied Sensor Research & Development Corporation (ASR&D) "NASA Acoustic Sensor Discussion", Oct. 11, 2006.
Brian Fisher, "Surface Acoustic Wave (SAW) Cryogenic Liquid and Hydrogen Gas Sensors", 2012, Electronic Theses and Dissertations, 2438, University of Central Florida.

* cited by examiner

METHOD OF FORMING SURFACE ACOUSTIC WAVE TAG-BASED GAS SENSORS

CROSS REFERENCE TO RELATED APPLICATIONS

This divisional application claims the benefit of Non-Provisional application Ser. No. 13/780,098 entitled "PASSIVE, WIRELESS, SURFACE ACOUSTIC WAVE IDENTIFICATION TAG WITH HYDROGEN GAS SENSOR", filed on Feb. 28, 2013, now U.S. Pat. No. 9,383,340 which is herein incorporated by reference in its entirety.

FIELD

This invention relates to surface acoustic wave devices and, in particular, to methods, systems and devices for passive, wireless, surface acoustic wave identification tags with a tin-oxide and palladium thin film that provides hydrogen gas sensor in the propagation path between the tag transducers and the frequency coded reflector banks.

BACKGROUND

Hydrogen gas is colorless, odorless, and not detectable by human senses. It is lighter than air and hence difficult to detect and is it not detectable by available infrared gas sensing technology. Coupled with the challenge of detection are the safety risks posed by the gas itself.

Hydrogen gas molecules are small and can diffuse through many materials considered airtight. Constant long-term exposure to hydrogen causes a phenomenon known as "hydrogen embrittlement" in many materials including metals and plastics. Embrittlement reduces the ductility and tensile strength of containment vessels to the point of fracture and eventual rupture and makes hydrogen more difficult to contain than other gasses. A form of hydrogen embrittlement takes place by chemical reaction. At high temperatures, hydrogen reacts with one or more components of metal walls to form hydrides, which weaken the atomic lattice.

Hydrogen gas is colorless, odorless, and not detectable by human senses. It is lighter than air and hence difficult to detect where accumulations cannot occur, and is it not detectable by infrared gas sensing technology. Coupled with the challenge of detection are the safety risks posed by the gas itself. At 1 atm, fire hazards exist for $H_2$—$O_2$ mixtures between the lower flammability limit (LFL) of 4% and upper flammability limit (UFL) of 94% $H_2$ by volume. In air, the lower and upper flammability limit of $H_2$ is 4.1% and 75% $H_2$ by volume, respectively, as shown in FIG. 7 because the $O_2$ composition of air is only 21%.

The lower and upper flammability limit and is also temperature dependent. The minimum ignition energy required to ignite hydrogen gas is between only 0.017 mJ to 1 mJ at 1 atm depending on hydrogen gas concentration in air, and decreases as temperature is increased. In comparison, the typical static electric discharge caused by humans in normal activity and industrial machinery lie the range of 1-100 mJ, thus, all personnel in an enclosed area must be evacuated before the hydrogen concentration in air reaches the lower flammability limit.

Current commercially available hydrogen gas detection technologies include catalytic, thermal conductivity, electromechanical, resistance based technology, work-function based technology, and optical detectors. Of the commercially available sensor technologies, only resistance and work-function based technologies can be integrated with a compact low-power wireless platform. Acoustic technologies can also be implemented in a passive, wireless configuration, however, none are commercially available.

The operating temperature of solid-state gas sensors is in the range of 50 to 150° C. and is not as hazardous as a catalytic bead sensor. However, the probability of spark discharges increases as humidity decreases and for a given moisture content, humidity is approximately halved for a 10 degree rise in temperature. This suggests that a sensor that operates at elevated temperatures increases the probability of hydrogen combustion via decreasing the minimum ignition energy, the lower flammability limit and increasing the probability of spark discharge.

Another problem with prior art sensor technologies is reversible detection of hydrogen gas at room temperature is difficult because the activation energy required to desorb the hydrogen gas from the sensitive film is a high temperature. Most commercially available hydrogen gas sensors use localized heaters that control the operating temperature, which is typically greater than 300° C. for catalytic bead gas sensors and 50 to 150° C. for solid-state gas sensors. The localized heaters require relatively high constant current, which translates to a limited battery life of the sensor.

The use of surface acoustic wave (SAW) devices as sensors was introduced in the 1970's. The first SAW-based hydrogen sensor was demonstrated by D'Amico et al. in 1982. D'Amico utilized SAW single and dual delay line oscillators in order to observe the frequency shift due to mass loading caused by a thick palladium (Pd) film in a range of 1900-7600 Å in the delay path. The fractional change in frequency was found to be proportional to film thickness. The reaction rates ranged from 0.8 to 21 Hz per second depending on gas concentration and flow rate.

Jakubik et al. also implemented a SAW dual delay line oscillator for hydrogen gas sensing, with the distinction of using a bilayer structure in the delay path. The bi-layer structure included a 1200 Å dielectric film consisting of copper phthalocycanine, (CuPc), nickel phthalocycanine, (NiPc), or metal-free phthalocycanine, ($H_2$Pc). The structure was placed between the SAW substrate and a 200 Å Pd film. The dielectric prevented the Pd film from shorting out the acoustoelectric response of the SAW. The mass loading effect of hydrogenated CuPc, NiPc, and $H_2$Pc and 200 Å Pd films are small when compared to the electrical response, thus, the acoustoelectric response is the dominant sensing mechanism.

The devices designed by D'Amico and Jakubik are active and wired and comprise a majority of the SAW-based hydrogen sensing designs found in literature.

A third example is the ball SAW device described in K. Yamanaka, et al., "Ball SAW Device For Hydrogen Gas Sensor," presented at the IEEE Ultrasonics Symposium, 2003. Like D'Amico, the ball sensor used a 200 Å Pd film in the SAW propagation path. Although, the ball sensor could be configured as a wireless device, the design was relatively complex and expensive to fabricate.

Wireless hydrogen sensors have been demonstrated by Y.-S. Huang, Y.-Y. Chen, and T.-T. Wu, "A passive wireless hydrogen surface acoustic wave sensor based on Pt-coated ZnO nanorods," Nanotechnology, vol. 21, 2010 used a $H_2$ sensitive resister to modulate a fraction of energy that is reflected by the SAW interdigitated transducer when the resister was exposed to hydrogen gas. Problems associated with Huang H2 sensors include long response time and the devices were not coded, thus when more than one was used, there was no way to distinguish one from another.

Other know hydrogen detectors include U.S. Pat. No. 7,268,662 issued to Hines, et al., on Sep. 11, 2007 which teaches use of a palladium nanocluster thin film deposited on the monolayer an interdigital SAW transducer to cause a modification of a response signal due to a change in conductivity of the palladium film when exposed to hydrogen; and U.S. Pat. No. 7,047,792 issued to Bhethanabotla, et al., on May 23, 2006 teaches nanoparticles or nanowires of palladium and metal free pthalocyanine coated on a lithium niobate substrate of a SAW device delay line.

Articles and papers on the subject include Goutam De, et al, Nanocrystalline mesoporous palladium activated tin oxide thin films as room temperature hydrogen gas sensors, from The Royal Society of Chemistry, 2007 which reports a surfactant-directed assembly approach to form high surface area mesoporous Pd-doped $SnO_2$ films exhibiting an interconnected nanocrystalline structure and high sensitivity for hydrogen gas at room temperature. Another paper by S. Kasthurirengan, et al., Palladium doped tin oxide based hydrogen gas sensors for safety applications AIP Conf. Proc. 1218, 1239 (2010) discloses development of Pd-doped tin-oxide-based hydrogen gas sensors.

The problems associated with the known devices described above can be mitigated by the implementation of a wireless, room-temperature hydrogen gas detection system, which continuously monitors multiple nodes and reports temperature and hydrogen gas presence. The ideal solution to the problems includes SAW device coding to determine which SAW device in a multi-tag system detects the hydrogen.

SUMMARY OF THE INVENTION

An objective of the present invention is to provide methods, systems and devices for a wireless surface acoustic wave (SAW) radio frequency device with a hydrogen gas sensor coupled in the propagating delay path between the SAW reflector bank and the transceiver. Another objective is to provide methods for creating a hydrogen sensor comprising a tin doxide (SnO2) film with a thin palladium (Pd) film thereon that is sensitive to hydrogen gas at room temperature for use with SAW identification tags by placing the hydrogen sensor in the delay path of the SAW tag.

Another objective is to provide methods, systems and devices for a wireless hydrogen gas sensor via the integration of the Pd film on the SnO2 film with the orthogonal frequency coded (OFC) SAW platform. Yet another objective is to provide methods, systems and devices for a low power or battery less, wireless SAW radio frequency device with a hydrogen gas sensor.

One embodiment is a method for fabricating a sensor system including providing a SAW tag on a substrate including a detector bank of reflectors at one end of the substrate to generate a detector SAW responsive to an interrogation signal, a reference bank of reflectors at an opposite end of the substrate to generate a reference SAW responsive to the interrogation signal. A transducer is between the detector and reference banks of reflectors for receiving the interrogation signal and transmitting the detector SAW and the reference SAW from the detector and the reference banks of reflectors in response. A hydrogen gas sensor is formed on the substrate in a propagation delay path between the detector bank of reflectors and the transducer to modulate propagation parameters of the detector SAW in response to sensing hydrogen gas. The forming includes depositing a $SnO_2$ film then depositing a Pd film onto the $SnO_2$ film.

The method can include providing a shadow mask having an aperture to expose the delay path before depositing the $SnO_2$ film, wherein the depositings are through the shadow mask. The depositings generally comprise chemical vapor deposition in a chamber. The annealing can comprise annealing at a temperature between 250° C. and 450° C.

The thickness of the SnO2 film can be 150 to 350 Å film and the thickness of the Pd film from 10 to 50 Å. The shadow mask can comprise a copper foil with the aperture being in the copper foil with an aperture size of 100 to 500 μm. The depositing the SnO2 film step can comprise evacuating the chamber to a pressure less than $3\times10^{-6}$ Torr, controlling a temperature of the substrate from 40 to 100° C., and controlling an O2 pressure to from $5\times10^{-6}$ to $1\times10^{-5}$ Torr in the chamber. The depositings can comprises using an electron beam evaporation process.

The reference bank of reflectors and the detector bank of reflectors can each provide a plurality of center frequencies to implement OFC SAW identification for use in a multi-sensor environment. The modulating of the detector SAW propagation parameters comprise modulation of an amplitude and delay of a second correlation peak of the detector SAW in the event of hydrogen gas detection. The reference bank of reflectors can be identical to the detector bank of reflectors.

DESCRIPTION OF THE PREFERRED EMBODIMENTS

Figure 1:
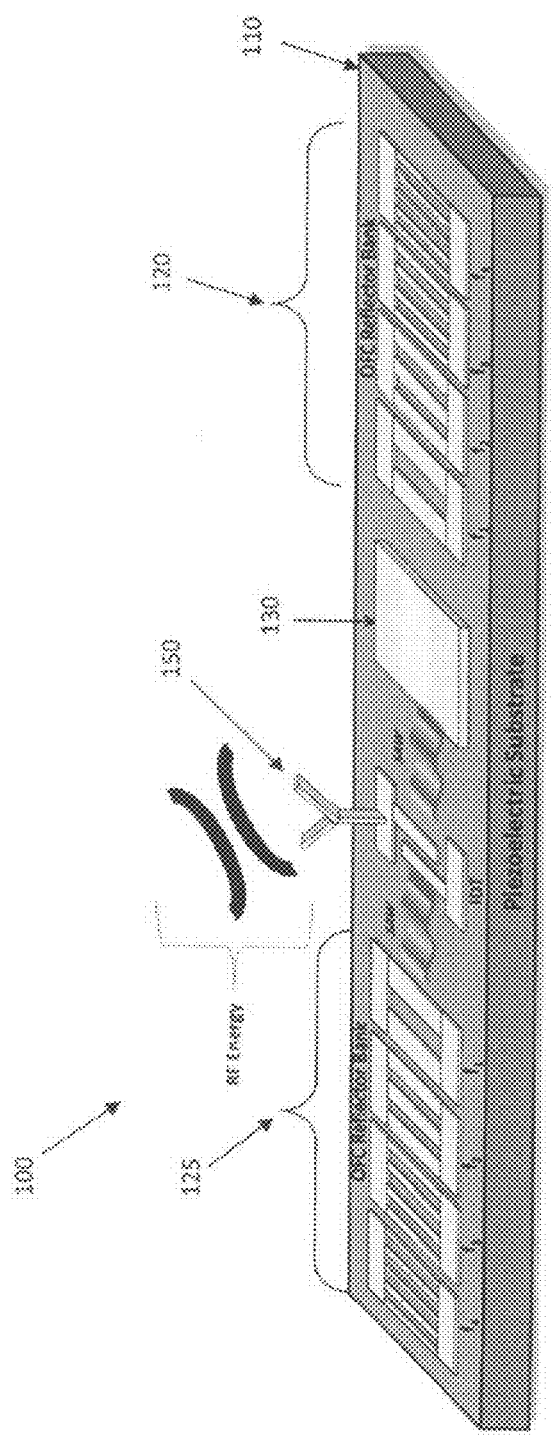
FIG. 1 is a perspective schematic diagram of a passive, wireless, OFC SAW identification tag sensor, according to an embodiment of the present invention.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The following is a list of reference numerals used in the description and the drawings to identify respective components:

100 SAW device
110 piezoelectric substrate
120 OFC reflector bank
125 reference OFC reflector bank
130 H2 sensor
150 transducer
200 film deposition system
210 sample holder
220 SAW device
230 shadow mask
250 vaporized film molecules
260 crystal monitors
270 electron beam
280 metal source
290 feedthroughs Inventor Malocha has completed research in the area of surface acoustic wave devices resulting in several issued U.S. Patents including U.S. Pat. Nos. 8,169,320; 7,961,105; 7,952,482; 7,825,805; 7,777,625; 7,642,898; and 7,623,037 and pending patent applications including U.S. Patent Pub. Nos. 2012/0174678 and 2011/0285510 each having a common inventor and assigned to the same assignee, and are each incorporated herein by reference in their entirety.

The OFC-SAW tag can be built on the commonly used YZ-lithium niobate (YZ-LiNbO3) piezoelectric substrate, a well-researched SAW device platform, and implements spread spectrum coding in order to achieve multiple-access capability to read multiple devices simultaneously.

In 2010 Inventor Malocha and B. H. Fisher completed a study on the Aging of Ultra-Thin Palladium Films on SAW Hydrogen Gas Sensors at the University of Central Florida, School of Electrical Engineering and Computer Science and concluded that ultra-thin Pd films suffer from oxygen adsorption when exposed to ambient air. The results of the study provided promising solutions to the aging problem, such as encapsulation and film annealing. These solutions may accelerate the practical implementation of passive, wireless, SAW hydrogen gas sensors in various environments.

They also completed a study of the acoustoelectric effect of SAW sensors that was published March 2010, entitled Ultrasonics, Ferroelectrics and Frequency Control, IEEE Transactions that described Pd resistivity verses thickness characterization and the effects of the SAW-Pd thin film interaction with and without hydrogen exposure. For this study, a series of test devices were designed and fabricated.

SAW-thin-film acoustoelectric in-situ observations and measurements were described at the 2011 Joint conference if the IEEE International conference May 2-5, 2011 by Dr. Malocha and Brian Fisher. This paper presented the approach taken in configuring an electron beam evaporation system for ultra-thin-film characterization and the design of test fixtures, data acquisition configuration, and experimental procedures to extract and analyze SAW parameters in real time, and to extract the thin-film properties under test. The paper also mentioned the discrepancy in measurement due to non-uniform distribution of the film.

The in-situ test fixture was designed to be mechanically, thermally and electrically stable. Data was taken for many SAW devices and over a wide range of frequencies and the results showed that the use of the in-situ procedure yielded: good agreement between theoretical predictions and the measured data, allowed characterization of a SAW hydrogen gas sensor in real-time and allowed various different methods to be used to calibrate the film deposition system and procedure.

The thin-film acoustoelectric effect in surface acoustic wave devices describes the interaction of electrical energy between a SAW in a piezoelectric medium and a thin-film placed in the wave's propagation path. The real-time observation of the thin-film acoustoelectric interaction is useful in the design and characterization of SAW-based thin-film chemical and physical sensors such as temperature, humidity, viscosity, voltage, current, Hall effects, and the like.

The present invention provides a wireless SAW radio frequency device with a hydrogen gas sensor deposited on the delay path between the SAW reflector bank and the transceiver. An embodiment provides methods for creating a tin dioxide ($SnO_2$) with palladium (Pd) film thereon stack that is sensitive to hydrogen gas at room temperature for use with the SAW identification tags.

Another embodiment provides methods and devices for a wireless hydrogen gas sensor via the integration of the Pd on $SnO_2$ film with the OFC-SAW platform. Advantages of the methods, systems and devices include a low power or battery less, wireless surface acoustic wave radio frequency device with a hydrogen gas sensor that uses OFC for use in a multi-tag system.

The first embodiment describes the creation of a passive (battery less), wireless, SAW device with an integrated hydrogen gas sensor that utilizes a room-temperature hydrogen sensitive Pd on $SnO_2$ film. In the preferred embodiment, the hydrogen gas sensors are built on a platform technology referred to as OFC-SAW radio frequency identification (RFID) tag sensors.

Orthogonal frequency coding the SAW identification tags and sensors enables unique sensor identification for use in a multi-sensor environment. Orthogonal frequencies are used to spread the signal bandwidth. The orthogonality condition describes a relationship between the local chip frequencies and their bandwidths wherein the adjacent frequencies are not required to be sequential. The OFC-SAW tag can be on the commonly used YZ-lithium niobate (YZ-LiNbO3) piezoelectric substrate 110, a well-researched SAW device platform, and implements spread spectrum coding in order to achieve multiple-access capability to read multiple devices simultaneously. A more complete description of orthogonal frequency coding can be found in U.S. Pat. No. 7,642,898 and in D. C. Malocha, et al., "Orthogonal frequency coding for SAW device application," 2004 IEEE International Ultrasonics, Ferroelectrics, and Frequency Control 50.sup.th Anniversary Joint Conference, in press, which are incorporated herein by reference.

FIG. 1 is a perspective schematic diagram of a passive, wireless, OFC-SAW identification tag hydrogen sensor 100 according to an embodiment of the present invention. In the example shown, the OFC reflector bank 120 is composed of sequential reflectors (called chips) with center frequencies from $f_1$ to $f_4$. The frequencies ($f_1$-$f_4$) are orthogonal in time and frequency to each other to minimize interference between chips as the SAW travels beneath the reflector bank. For hydrogen gas sensing, a Pd—$SnO_2$ film 130 is deposited in the delay path between the SAW transducer 150 and the OFC reflector bank 120. Another identical OFC reflector bank 125 on the other side of the SAW transducer 150 is used as a reference for sensing changes.

Figure 2:
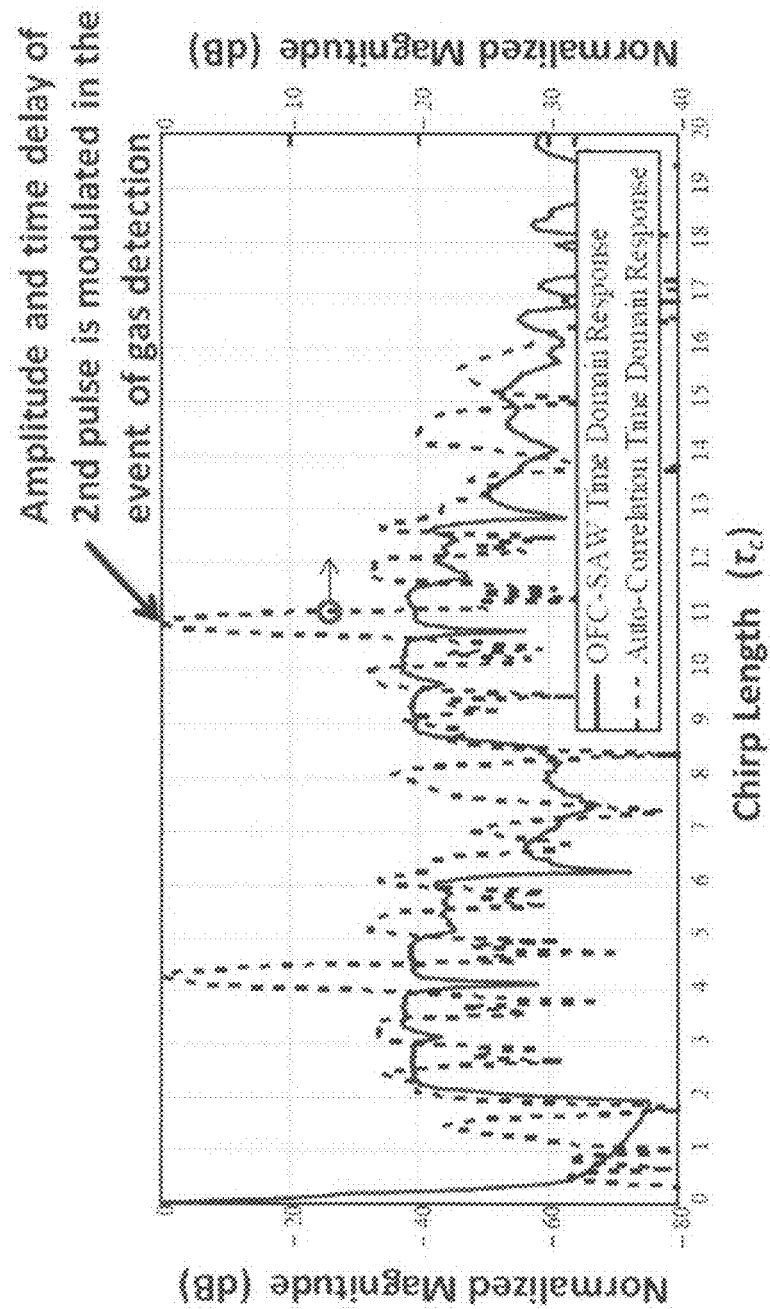
FIG. 2 shows the normalized magnitude (in dB) of an OFC SAW time domain response showing the modulation of a pulse in response to hydrogen gas detection.

The SAW propagation parameters are modulated by the presence and the properties of the chemically-sensitive thin-film and the amplitude and delay of the second correlation peak is modulated in the event of gas detection. The received OFC-SAW signal is correlated against a matched filter producing two compressed pulses; one pulse remains unchanged on exposure to hydrogen gas, while the other exhibits changes in insertion loss and delay, due to acoustoelectric interaction of hydrogen gas with the Pd—SnO$_2$ film and the SAW as shown in FIG. 2.

Figure 3:
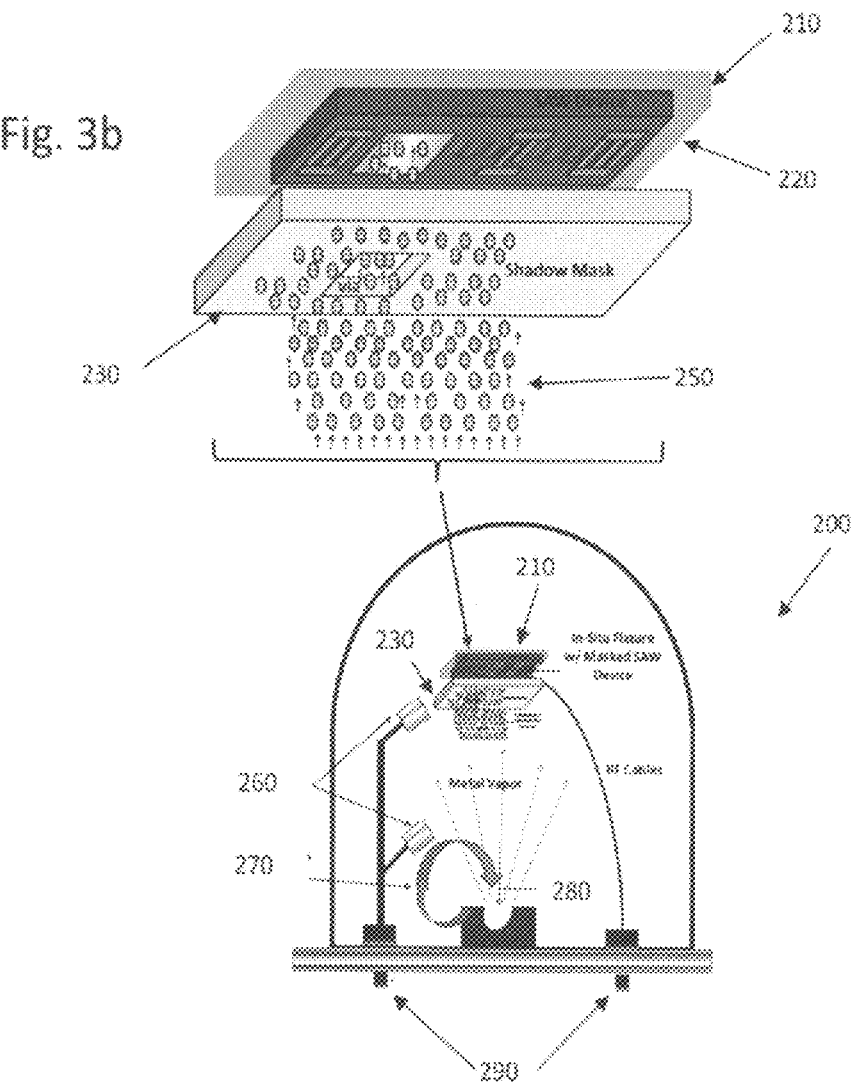
FIG. 3a shows a schematic of the in-situ fixture with a masked SAW device inside the e-beam film deposition system.
FIG. 3b is an exploded view of the SAW device, shadow mask and the evaporation film molecules.

A second embodiment describes the development of a room-temperature hydrogen sensitive tin dioxide (SnO$_2$) and palladium (Pd) film. FIG. 3a shows a schematic of the in-situ fixture 200 with a masked SAW device 220 inside the electron-beam film deposition system 200, with dual quartz crystal monitors 260, and high-vacuum RF feed through 290. The metal source is 280.

FIG. 3b is an exploded view of the SAW device 220 on the sample holder 210 connected with an RF cable, shadow mask 230 and the evaporation film molecules 250. As shown, an electron beam 270 is applied to the metal source 280 causing metal vapors directed toward the masked saw device 220.

The growth and processing of the Pd—SnO2 is important to its reversibility, sensitivity and room-temperature operation when exposed to hydrogen gas. Pd—SnO$_2$ with non-uniform thickness profiles were created by vapor deposition through a shadow mask 230 as shown in FIG. 3a and annealed for approximately 5 min at approximately 350° C. in order to gain room-temperature hydrogen sensitivity and reversibility. The method produced a non-uniform approximately 250 Å SnO$_2$ film with approximately 20 Å of Pd having a rapid, stable response to hydrogen gas.

The shadow mask 230 was made from a 100 to 500 μm thick copper foil with an approximately 100 to 500 μm aperture width to ensure that the signal was not buried in noise at maximum attenuation at 915 MHz. The distance between the aperture and the substrate was approximately 2 mm. Experimentation on films of uniform thickness-profiles failed to produce the long-term stability. Hydrogen sensitivity and reaction rates were observed in the non-uniform film profiles.

SnO$_2$ film depositions were performed using an electronic beam evaporator with 99.9% pure pellets, which were purchased from Kurt J Lesker Company. The material was evaporated from an Al$_2$O$_3$ crucible liner using approximately 10 kV and approximately 28 to 32 mA of current. The evaporation current was relatively low because SnO$_2$ sublimes and creates very high deposition rates at relatively low currents. High deposition rates are known to create porous films which are desired for gas sensing but provide poor control over the desired thickness.

The SnO$_2$ depositions were kept in a range between approximately 3 to 5 Å/s to ensure reproducibility. A substrate temperature controller and oxygen gas injection were used on the ebeam system to control the deposition environment as precisely as possible. Elevating the substrate temperature has the added benefit of desorbing surface adsorbed molecules that survive the substrate cleaning process.

The substrate temperature was controlled at approximately 60° C. and an oxygen pressure of approximately $3 \times 10^{-5}$ Torr was introduced after the chamber was evacuated to less than approximately $3 \times 10^{-6}$ Torr. The O$_2$ gas was evacuated before the Pd ultra-thin film (UTF) of 10 to 50 Å was evaporated. For the purposes in the experiment, the Pd UTF film needed to be as porous as possible, thus the slowest stable growth attainable of approximately 0.1 Å/s was used. The Pd UTF film was evaporated from a tungsten crucible liner using approximately 10 kV and approximately 40 mA of current.

Figure 4:
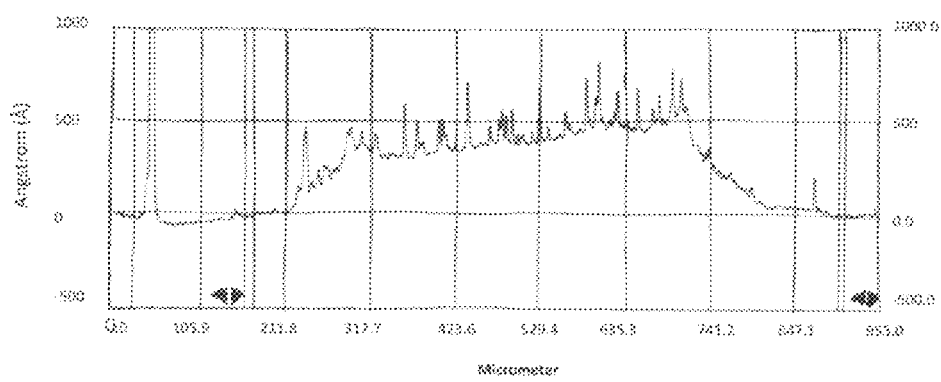
FIG. 4 shows a non-uniform film thickness profile after deposition through a shadow mask.

After deposition and annealing the film's thickness profile was measured using Veeco Dektak Stylus profilometer. FIG. 4 shows an approximately 500 Å SnO2+20 Å Pd film thickness profile after deposition through an approximately 0.5 mm aperture shadow mask. The film thickness profile was found to be non-uniform as shown in FIG. 4. The slope in the side walls were found to follow a Gaussian distribution and the top was flat. The packaged sensor die was soldered to a planar 915 MHz folded dipole antenna.

Figure 5:
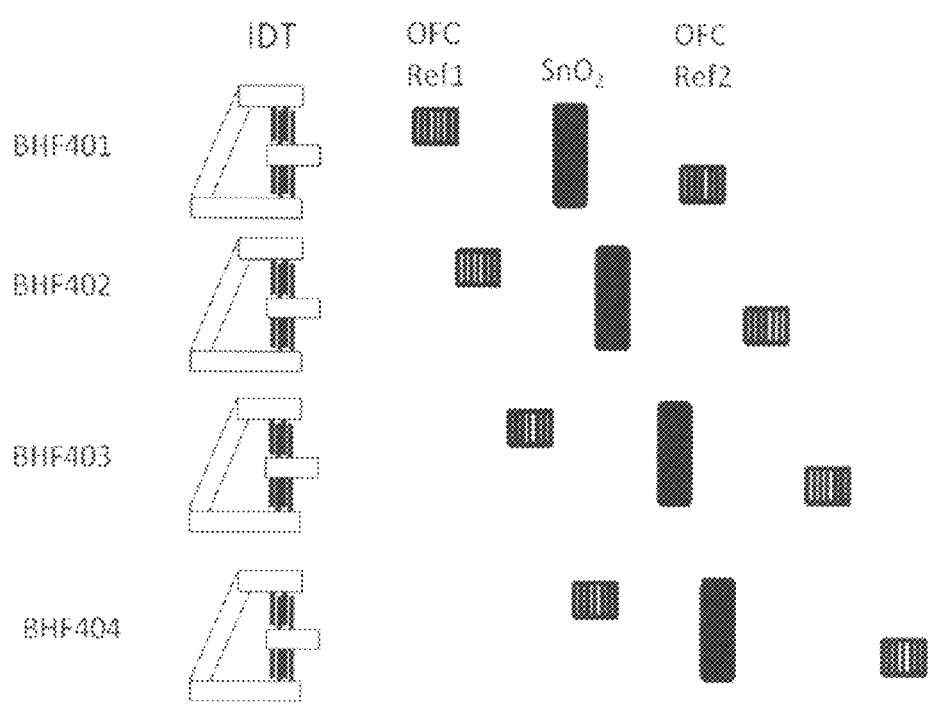
FIG. 5 is a schematic showing four different orthogonal frequency codes.

FIG. 5 is a schematic of four different OFC-SAW codes, labeled as BF401 through BF404 that were created for testing. The three devices labeled BHF402, BF403 and BHF404 where simultaneously interrogated from a distance of approximately 1.5 feet while they were exposed to various flow rates of 2% H$_2$, 98% N$_2$ gas. For the experiment, three sensors were placed directly above the gas flow tubes to benefit from the buoyancy of hydrogen gas and to increases the chances of exposure at low flow rates.

Figure 6A:
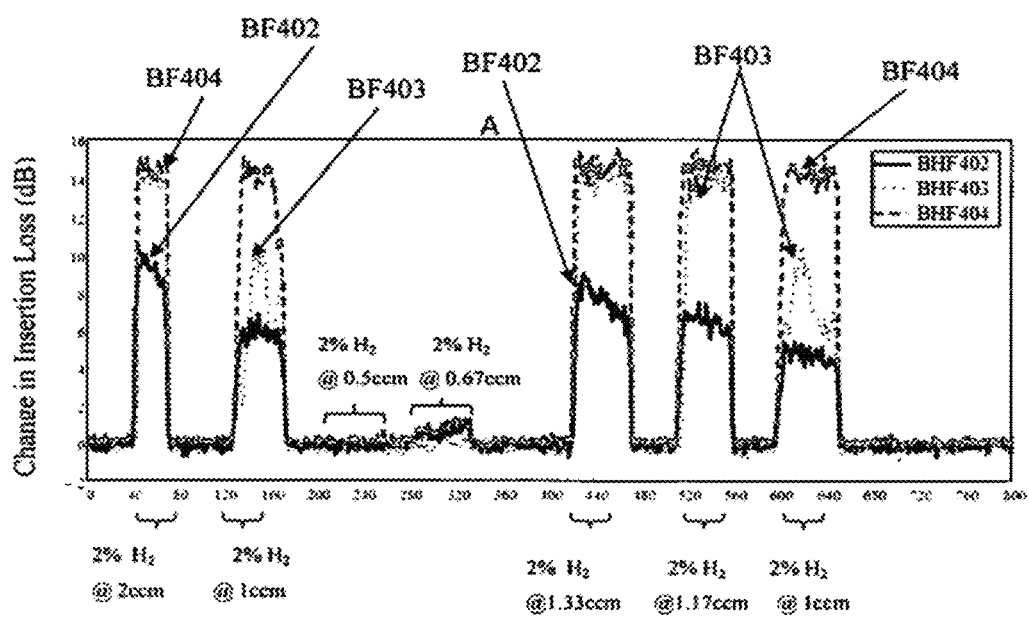
FIG. 6a shows a plot of the change in propagation loss as a function of time for 3 passive wireless OFC-SAW devices.

The transmitting/receiving (Tx/Rx) antenna was placed above the sensors. In the absence of a gas mixing equipment the sensors were exposed to various flow rates of hydrogen gas. This is equivalent to exposing the film to various concentrations of hydrogen gas because the number of hydrogen molecules that react with SnO$_2$ changes with flow rate and gas concentration. The change in propagation loss and the fractional change in group delay of the sensors BF402, BF403 and BF404 are plotted in FIG. 6a. Upon exposure to 2% H2 98% N2 gas there was a 10 dB (BHF402) to 15 dB (BHF403 & BHF404) increase in propagation loss in the devices. BHF402 is used to determine the amplitude sensitivity because BHF403 and BHF404 become saturated at relatively low flow rates.

Figure 6B:
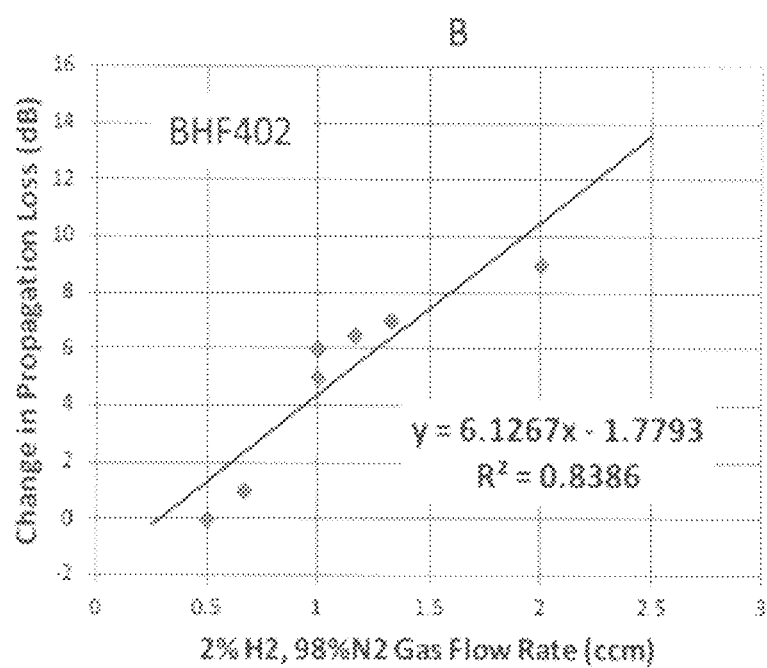
FIG. 6b is a plot showing the linear relationship between the change in insertion loss as a function of hydrogen gas flow rate.
Figure 7:
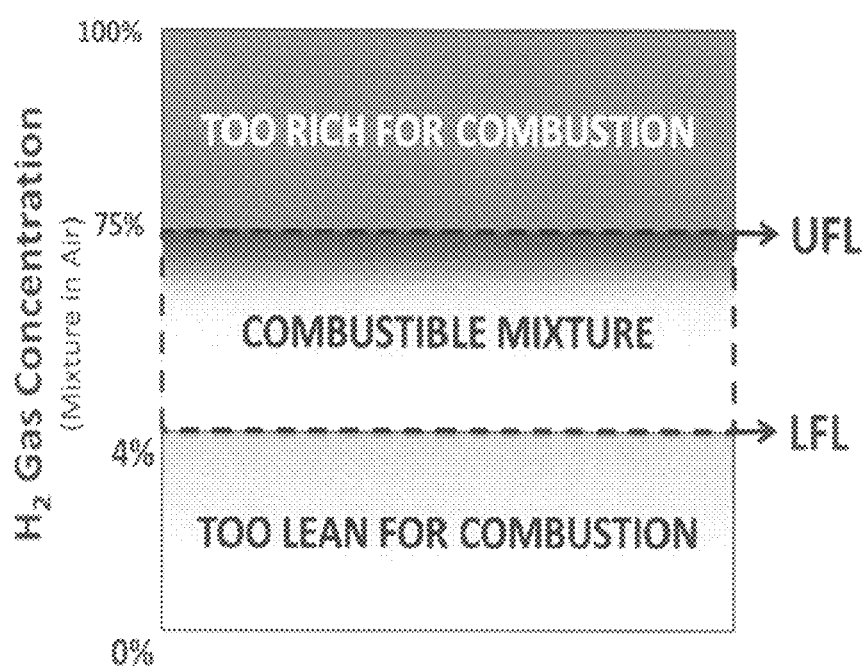
FIG. 7 shows the upper and lower flammability limits of hydrogen by volume in air.

FIG. 6b is a plot of the change in propagation loss as a function of the flow rate of 2% H2 98% N2 gas. It shows a linear relationship between the change in propagation loss as a function of gas flow rate for BHF402. This shows that the sensors can have a linear response to various concentrations of hydrogen gas. Given the high fractional change at relatively low flow rates, the sensors may utilized for low concentrations (in hundreds of ppm range) of hydrogen in order to prevent saturation and to observe a linear response.

Referring back to FIG. 1, the Pd—SnO$_2$ film 130 just described is deposited in the delay path between the SAW transducer 150 and the OFC reflector bank 120. The SAW propagation parameters are modulated by the presence and the properties of the chemically-sensitive Pd on SnO$_2$ film and the amplitude and delay of the second correlation peak is modulated when hydrogen gas is detected. The received OFC-SAW signal is correlated against a matched filter producing two compressed pulses; one pulse remains unchanged on exposure to hydrogen gas, while the other exhibits changes in insertion loss and delay, due to acoustoelectric interaction of hydrogen gas with the Pd—SnO$_2$ film and the SAW as shown in FIG. 2.

The methods and devices of the present invention can be used to make wireless distributed measurements of the presence and concentration of hydrogen gas in an area. The U.S. Department of Energy has expressed a need for high-temperature selective gas sensors for down-stream process monitoring of hydrogen gas in fossil energy power systems.

Areas having an existing need for the sensors according to the present invention are in nuclear reactors containment buildings, oil refineries, coal mines, and process plants. Within the energy industry, power transmission and distribution equipment would benefit from continuous distributed monitoring since power transmission and distribution equipment failure is typically preceded by temperature anomalies and discharge of gaseous hydrocarbons. This can result in higher efficiency and lower costs to the consumer. The nuclear power industry has also expressed interest in the use of radiation hard passive wireless hydrogen gas sensor networks in reactor containment tanks. Excessive hydrogen levels can be used to indicate depletion of the cooling water. NASA has also expressed needs for passive wireless hydrogen gas sensing networks that can determine the concentration of location of a gas leak at various ground support and research facilities.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

The invention claimed is:

1. A method for fabricating a sensor system, comprising:
 providing a surface acoustic wave (SAW) tag on a substrate, the SAW tag including a detector bank of reflectors at one end of the substrate to generate a detector SAW in response to an interrogation signal, a reference bank of reflectors at an opposite end of the substrate to generate a reference SAW in response to the interrogation signal, and a transducer on the substrate between the detector and reference banks of reflectors for receiving the interrogation signal and transmitting the detector SAW and the reference SAW from the detector and the reference banks of reflectors in response, and
 forming a hydrogen gas sensor on the substrate in a propagation delay path (delay path) between the detector bank of reflectors and the transducer to modulate propagation parameters of the detector SAW in response to sensing hydrogen gas, wherein the forming comprises:
 depositing a tin-dioxide ($SnO_2$) film onto the delay path;
 depositing a palladium (Pd) film onto the $SnO_2$ film, wherein a thickness of the $SnO_2$ film is 150 Å to 350 Å and a thickness of the Pd film is 10 Å to 50 Å, and annealing the hydrogen gas sensor.

2. The method of claim 1, wherein the forming further comprises:
 providing a shadow mask having an aperture to expose the delay path before depositing the $SnO_2$ film, wherein the depositings are through the shadow mask.

3. The method of claim 1, wherein the depositings comprise chemical vapor deposition in a chamber.

4. The method of claim 1, wherein the annealing comprises annealing at a temperature between 250° C. and 450° C.

5. The method of claim 2, wherein the shadow mask comprises a copper foil with the aperture being in the copper foil with an aperture size of 100 to 500 μm.

6. The method of claim 3, wherein the depositing the $SnO_2$ film step comprises:
 evacuating the chamber to a pressure less than $3\times10^{-6}$ Torr;
 controlling a temperature of the substrate from 40 to 100° C., and
 controlling an $O_2$ pressure to from $5\times10^{-6}$ to $1\times10^{-5}$ Torr in the chamber.

7. The method of claim 6, wherein the depositings comprise using an electron beam evaporation process.

8. The method of claim 1, wherein the reference bank of reflectors and the detector bank of reflectors each provide a plurality of center frequencies to implement orthogonal frequency coded SAW identification for use in a multi-sensor environment.

9. The method of claim 1, wherein the modulate of the detector SAW propagation parameters comprise modulation of an amplitude and delay of a second correlation peak of the detector SAW in the event of hydrogen gas detection.

10. The method of claim 1, wherein the reference bank of reflectors are identical to the detector bank of reflectors.

* * * * *